(12) United States Patent
Morshead et al.

(10) Patent No.: US 9,968,782 B2
(45) Date of Patent: May 15, 2018

(54) SELECTIVE, DIRECTABLE ELECTROTAXIS OF PRECURSOR CELLS WITH BIPHASIC ELECTRICAL STIMULATION

(71) Applicant: THE GOVERNING COUNCIL OF THE UNIVERSITY OF TORONTO, Toronto, Ontario (CA)

(72) Inventors: Cindi M. Morshead, Toronto (CA); Milos R. Popovic, Mississauga (CA); Robart Babona-Pilipos, Toronto (CA)

(73) Assignee: The Governing Council of the University of Toronto, Toronto (CA)

( * ) Notice: Subject to any disclaimer, the term of this patent is extended or adjusted under 35 U.S.C. 154(b) by 0 days. days.

(21) Appl. No.: 15/122,109

(22) PCT Filed: Feb. 27, 2015

(86) PCT No.: PCT/CA2015/050148
§ 371 (c)(1),
(2) Date: Aug. 26, 2016

(87) PCT Pub. No.: WO2015/127560
PCT Pub. Date: Sep. 3, 2015

(65) Prior Publication Data
US 2017/0072201 A1    Mar. 16, 2017

Related U.S. Application Data

(60) Provisional application No. 61/946,122, filed on Feb. 28, 2014.

(51) Int. Cl.
| A61N 1/36 | (2006.01) |
| A61N 1/32 | (2006.01) |
| C12N 5/079 | (2010.01) |
| C12N 5/0793 | (2010.01) |
| G01N 33/50 | (2006.01) |

(52) U.S. Cl.
CPC ......... *A61N 1/36103* (2013.01); *A61N 1/326* (2013.01); *A61N 1/36171* (2013.01); *A61N 1/36175* (2013.01); *C12N 5/0618* (2013.01); *C12N 5/0619* (2013.01);
(Continued)

(58) Field of Classification Search
None
See application file for complete search history.

(56) References Cited

U.S. PATENT DOCUMENTS 7,079,899 B2 * 7/2006 Petrofsky ............... A61N 1/326
607/50
7,117,034 B2 * 10/2006 Kronberg ............... A61N 1/326
607/2
(Continued)

OTHER PUBLICATIONS

International Search Report & Written Opinion re PCT/CA2015/050148 dated May 14, 2015.
International Preliminary Report on Patentability re PCT/CA2015/050148 dated Sep. 6, 2016.
Jahanshahi, A. et al. (2013) Electrical stimulation of the motor cortex enhances progenitor cell migration in the adult rat brain. Experimental Brain Research, 231 165-177.
(Continued)

*Primary Examiner* — Brian T Gedeon
(74) *Attorney, Agent, or Firm* — C. Brandon Browning; Maynard, Cooper & Gale, PC (57) ABSTRACT

A method and system for enhancing migration of precursor cells in a desired direction, comprising applying a biphasic monopolar electrical field to the precursor cells. The method and system can be used to treat injury or disease of neural or skin tissue.

20 Claims, 7 Drawing Sheets

(52) U.S. Cl.
CPC ...... *A61N 1/36146* (2013.01); *C12N 2529/00* (2013.01); *G01N 33/5029* (2013.01); *G01N 33/5058* (2013.01)

(56) References Cited

U.S. PATENT DOCUMENTS

| | | | | |
|---|---|---|---|---|
| 8,014,854 | B2* | 9/2011 | Schroeppel | A61K 47/48992 604/20 |
| 8,367,410 | B2* | 2/2013 | Radisic | C12N 5/0658 435/173.1 |
| 9,044,611 | B2* | 6/2015 | Zhao | A61N 1/36103 |
| 9,295,850 | B2* | 3/2016 | Kallmyer | A61N 1/36125 |
| 2003/0088274 | A1* | 5/2003 | Gliner | A61N 1/36017 607/3 |
| 2009/0132003 | A1* | 5/2009 | Borgens | A61N 1/205 607/50 |
| 2009/0132010 | A1* | 5/2009 | Kronberg | A61N 1/32 607/72 |
| 2009/0232784 | A1* | 9/2009 | Feldman | A61K 35/44 424/93.21 |
| 2009/0259275 | A1 | 10/2009 | Wan | |
| 2011/0028859 | A1* | 2/2011 | Chian | A61B 5/04001 600/554 |
| 2014/0273218 | A1* | 9/2014 | Radojicic | A61L 27/227 435/375 |
| 2014/0350622 | A1* | 11/2014 | Freeman | A61N 1/3906 607/9 |

OTHER PUBLICATIONS

Kahle, M.P. et al. (2013) Neuronal Restoration Following Ischemic Stroke: Influences, Barriers, and Therapeutic Potential. Neurorehabilitation and Neural Repair, 27:5 469-478.

Babona-Pilipos, R. et al. (2012) A Galvanotaxis Assay for Analysis of Neural Precursor Cell Migration Kinetics in an Externally Applied Direct Current Electric Field. Journal of Visualized Experiments, 68:e4193.

Babona-Pilipos, R. et al. (2011) Adult Subependymal Neural Precursors, but Not Differentiated Cells, Undergo Rapid Cathodal Migration in the Presence of Direct Current Electric Fields. PloS ONE 6:8 E23808.

Reynolds, B., Weiss, S. (1992) Generation of Neurons and Astrocytes From Isolated Cells of the Adult Mammalian Central Nervous System. Science 255:5052 1707-1710.

Popovic, M.R. and Keller, T. (2005) Modular Transcutaneous Functional Electrical Stimulation System. Med Eng Phys, 27:1 81-92.

Biernaskie, J.A. et al. (2007) Isolation of Skin-Derived Precursors (SKPs) and Differentiation and Enrichment of Their Schwann Cell Progeny. Nature Protocols, 1:6 2803-2812.

Richards, L.J. et al. (1992) De Novo Generation of Neuronal Cells From the Adult Mouse Brain. Proc. Natl. Acad. Sci. USA, 89 8591-8595.

* cited by examiner

SELECTIVE, DIRECTABLE ELECTROTAXIS OF PRECURSOR CELLS WITH BIPHASIC ELECTRICAL STIMULATION

BACKGROUND OF THE INVENTION

Precursor cells, such as neural precursor cells, have recently been shown to generate and grow, well into adulthood, in the mammalian brain and elsewhere. This finding has altered our understanding of neuroplasticity and skin plasticity and our outlook on repairing injured tissue, such as injured brain and skin, following injury or disease.

Adult neural precursor cells (NPCs) reside in two neurogenic regions in the forebrain: the subependyma lining the lateral ventricles (SEZ) and the subgranular zone (SGZ) of the hippocampal dentate gyrus. Under baseline conditions, SEZ NPCs give rise to neuroblasts that migrate along a well defined pathway known as the rostral migratory stream toward the olfactory bulb, where they differentiate into interneurons. The inherent properties of proliferation, migration and neurogenesis make SEZ NPCs good candidates for contributing to neurorepair following neural insult, such as stroke, with SEZ derived NPCs having already been shown in the literature to contribute to neurogenesis following injury.

Neural insult appears to cause upregulation of multiple chemical and physical cues that enhance NPC proliferation and induce the redirection of their migration toward the lesion site, as comprehensively reviewed by Kahle et al. (Neurorehabilitation and neural Repair, vol 27 p. 469-478, June 2013), incorporated herein by reference. However, the neuroregenerative impact of endogenous NPC activity is limited. The introduction of exogenous factors appears to somewhat enhance post-insult response by NPCs, and promote functional recovery, but long-term safety concerns have limited their clinical applicability. Targeting the recruitment of NPCs to appropriate areas remains a major challenge in neurorepair efforts, and the evolution of novel methods to direct their migration is instrumental to the development of successful neurorepair strategies.

Analogously, skin progenitor cells have been found to play a role in post-insult response to skin injury. These cells may also migrate towards an injury site, and are involved in healing and recovery.

Without being limited to any particular theory, in very basic terms, it is believed that progenitor cells naturally migrate to a site of injury, then proliferate and/or differentiate into the required cells to help with healing and tissue formation at the site of injury.

Endogenous direct current electric fields (dcEFs) appear to play an important role in physiological processes, including development, wound healing, nerve growth, and angiogenesis. In vitro, external application of dcEFs has been suggested in some cases to induce the directed migration of certain cell types toward either the anode or the cathode of the electric field in a process known as electrotaxis. For example, the present inventors have shown that dcEFs are able to induce rapid and directed cathodal electrotaxis of adult SEZ-derived NPCs, but not in differentiated populations (Babona-Pilipos et al., *Journal of Visualized Experiments*, (2012); Babona-Pilipos et al., PLOS ONE (2011); both incorporated herein by reference) making the application of direct current electric fields a possible approach to neuroregenerative strategies.

Direct current stimulation has many challenges, especially in clinical applications. Prolonged exposure to dcEFs results in charge accumulation at the electrode-tissue interface. Such charge build-up may cause electrode corrosion followed by the formation of toxic reactive oxygen species and subsequent, often significant tissue damage due to the electrochemical reactions that occur at the electrode-tissue interface. Moreover, excessive charge accumulation at the electrodes can impede the flow of current from the stimulating electrodes. Tissue damage is generally undesirable, but especially at the site at which tissue growth is desired.

It would be desirable to be able to differentially direct migration of precursor cells with an improved side effect profile.

Biphasic current stimulation provides a generally more desirable safety profile, since it avoids charge build up and the resultant tissue damage. However, to date, biphasic current stimulation has failed to provide directed electrotaxis.

SUMMARY OF THE INVENTION

According to one aspect of the invention is provided a method of enhancing migration of a precursor cell in a desired direction, comprising applying a biphasic monopolar electrical field having a cathode end and an opposing anode end to said neural precursor cell.

In certain embodiments, the precursor cell may be, for example, a skin derived precursor cell or a neural precursor cell.

In certain embodiments, the desired direction and said enhancement of migration occurs towards the cathode end. In other embodiments, it occurs towards the anode end.

In certain embodiments, the biphasic monopolar electrical field is a charge balanced biphasic monopolar electrical field.

In certain embodiments, the balanced biphasic monopolar electrical field comprises a negative phase and a positive phase, wherein the negative phase has a greater amplitude than the positive phase, and the positive phase has a greater duration than the negative phase, charge-balancing said greater amplitude of said negative phase. For example, in certain embodiments, the negative phase has about four times the amplitude and about one quarter the duration of the positive phase.

In certain embodiments, the negative phase and/or the positive phase are pulsatile phases. In other embodiments, the phases can be constant phases.

In certain embodiments, the negative phase has an amplitude of between 2-5 mA, for example, about 3 mA, and a pulse width of between 250-750 µs, for example, about 500 µs.

In certain embodiments, the negative phase yields an electric field strength of less than 500 mV/mm, for example, 150 to 350 mV/mm, or about 250 mV/mm.

In certain embodiments, the charge balanced biphasic monopolar electrical field has a frequency of between 100-1000 Hz, for example, about 400 Hz.

In certain embodiments, the charge balanced biphasic monopolar electrical field comprises a negative phase and a positive phase, wherein the positive phase has a greater amplitude than the negative phase, and the negative phase has a greater duration than the positive phase, charge-balancing said greater amplitude of said positive phase. For example, in certain embodiments, the positive phase has about four times the amplitude and about one quarter the duration of the negative phase.

In certain embodiments, the positive phase has an amplitude of between 2-5 mA, for example, about 3 mA, and a pulse width of between 250-750 μs, for example, about 500 μs.

In certain embodiments, the positive phase yields an electric field strength of less than 500 mV/mm, preferably 150 to 350 mV/mm, more preferably about 250 mV/mm.

In certain embodiments, the biphasic monopolar electrical field is an unbalanced biphasic monopolar electrical field.

In certain embodiments, the migration is specific to undifferentiated neural precursor cells, such that differentiated cells do not migrate in said desired direction when the field is applied.

In certain embodiments, the method may be applied in vitro. In other embodiments, the method may be applied in vivo, for example, by applying the electrical field through a portion of a central nervous system.

According to a further aspect of the present invention is provided a method of treating a disease or injury of a central nervous system of a patient, comprising: determining a location of an injured region within said central nervous system; determining a location of a source of neural precursor cells in said central nervous system; applying electrodes to said patient such that the distance between said electrodes form a path, said path transecting both the location of the source of neural precursor cells and the location of the injured region; then applying the method of enhancing migration as previously described to said central nervous system.

According to certain embodiments, the disease or injury of the central nervous system is stroke, spinal cord injury, traumatic brain injury or multiple sclerosis.

In certain embodiments, the portion of the central nervous system being applied to is the brain.

According to certain embodiments, the method further comprises, after applying the method of enhancing migration, determining the location of the neural precursor cells, for example, by introducing a marker for said neural precursor cells into said central nervous system, for example, into said brain.

According to certain embodiments, the method further comprises, any time after applying the method of enhancing migration, stimulating differentiation and/or survival of said neural precursor cells, for example, through administration of factors that promote neural differentiation, and/or cell survival, for example, the factors brain-derived neurotrophic factor, erythropoietin, insulin-like growth factor, nerve growth factor, ciliary neurotrophic factor, platelet derived growth factor TNF-alpha, TNF-beta, TNF-gamma, and stem cell factor.

According to a further aspect of the present invention is provided a method of treating a disease or injury of the skin tissue of a patient, comprising: determining a location of an injured region within said skin tissue; determining a location of a source of skin derived precursor cells in or proximal to said skin tissue; applying electrodes to said patient such that the distance between said electrodes form a path, said path transecting both the location of the source of skin derived precursor cells and the location of the injured region; applying the method of enhancing migration as previously described to said skin tissue.

According to certain embodiments, the disease or injury of the skin tissue is a skin lesion, bed sores, an acute wound, a chronic wound, a burn, or a diabetic pressure sore.

According to certain embodiments, the method further comprises, after step d, determining the location of the skin derived precursor cells, for example, by introducing a marker for said skin derived precursor cells into said skin tissue.

According to certain embodiments, the cells are endogenous. In other embodiments, the cells are allogenous. In certain embodiments, the cells are autogenous. In certain embodiments, the cells are isogenous.

According to a further aspect of the invention is provided a system for performing the method of any one of the preceding claims, comprising: an electrical stimulator configured to provide the biphasic monopolar electrical field; at least one anode connected to said stimulator by an electrical cable; at least one cathode connected to said stimulator by an electrical cable; whereby the anode and cathode are capable of being applied to said respective anode end and cathode end to provide the biphasic monopolar electrical field and enhancing the migration of the precursor cell.

According to a further aspect of the invention is provided a system for performing the method as herein described, comprising: an electrical stimulator configured to provide the balanced biphasic monopolar electrical field having the negative phase having a greater amplitude than the positive phase, and the positive phase with a greater duration than the negative phase, charge-balancing said greater amplitude of said negative phase; at least one anode connected to said stimulator by an electrical cable; at least one cathode connected to said stimulator by an electrical cable; whereby the anode and cathode are capable of being applied to said respective anode end and cathode end to provide the biphasic monopolar electrical field and enhancing the migration of the precursor cell.

According to a further aspect of the invention is provided a system for performing the method as herein described, comprising: an electrical stimulator configured to provide the balanced biphasic monopolar electrical field having the negative phase having an amplitude about four times the amplitude and about one quarter the duration of the positive phase; at least one anode connected to said stimulator by an electrical cable;

at least one cathode connected to said stimulator by an electrical cable;

whereby the anode and cathode are capable of being applied to said respective anode end and cathode end to provide the biphasic monopolar electrical field and enhancing the migration of the precursor cell.

According to a further aspect of the present invention is provided a system for performing the method as herein described, comprising: an electrical stimulator configured to provide the electric field strength of about 250 mV/mm; at least one anode connected to said stimulator by an electrical cable; at least one cathode connected to said stimulator by an electrical cable; whereby the anode and cathode are capable of being applied to said respective anode end and cathode end to provide the biphasic monopolar electrical field and enhancing the migration of the precursor cell.

In certain embodiments, the system as hereindescribed has an electrical stimulator that is implantable. In certain embodiments, the system has an anode that is implantable. In certain embodiments, the cathode is implantable.

DETAILED DESCRIPTION

Balanced biphasic electric fields are shown to induce rapid and directed electrotaxis in undifferentiated adult progenitor cells. This electrotaxis was selective for the undifferentiated adult progenitor cells, with identical electrical fields providing no electrotaxis of differentiated populations.

Because the electrotaxis is directed (i.e. moves in the direction of the electrical field), it can be used to direct undifferentiated progenitor cells to a desired location. For example, a directed electrical field can be used in situ within an organism to direct undifferentiated progenitor cells from their natural location within the organism to a desired location, for example, an injury site and/or a site where it is desirable to have undifferentiated progenitor cells. Once the cells migrate to the desired location, differentiation factors and/or growth factors can be used to multiply and differentiate the progenitor cells as desired. Alternatively or in addition to use of exogenous differentiation/growth factors, once the cells migrate to the desired location, one can rely on natural cell signaling and repair pathways to differentiate and multiply the cells as needed. For example, brain-derived neurotrophic factor (BDNF) plays a pro-survival role and promotes the growth and maturation of neurons (enhancing plasticity). Erythropoietin is a regulator of red blood cell production and is involved in angiogenesis. Following brain injury, erythropoietin has a neuroprotective and pro-survival effect, and promotes the differentiation of neural stem cell progeny to neurons. Insulin-like growth factor also plays a pro-survival and neuroprotective role, and regulates neuronal differentiation. Nerve growth factor is neuroprotective and pro-survival, and promotes axonal growth. Ciliary neurotrophic factor is pro-survival and promotes projection outgrowth in neuronal and glial cells. Platelet derived growth factor is neuroprotective and regulates the proliferation of oligodendrocyte progenitors and is thought to promote differentiaton of glial progenitors to an oligo phenotype. It is also a regulator of angiogenesis. Tumor necrosis factor family of cytokines are upregulated in the brain following injury, and are involved in mediating the inflammatory response. Stem cell factor is a pro-migratory and angiogenic cytokine that is upregulated in the brain following injury. It also promotes neuronal differentiation of NSCs.

Directed electrotaxis can also be utilized in vitro to separate undifferentiated progenitor cells from differentiated cells, to test whether a cell is differentiated, to investigate the mechanisms that mediate cellular migration, and to assay for the migratory capabilities of a cell population.

Although the Examples below are for neural precursor cells, the same principles apply to other precursor cells, such as skin precursor cells. Like the neural precursor cells shown here, undifferentiated skin precursor cells will also show rapid and directed, selective, electrotaxis in the presence of the herein described biphasic electric fields.

In addition to promoting electrotaxis, balanced biphasic stimulation may exert other beneficial effects on neural stem and progenitor cells, including the promotion of expansion and neuronal differentiation of fetal neural precursors, and the promotion of cell survival and anti-apoptotic effects in growth factor-depleted conditions through brain derived neurotrophic factor and phosphatidylinositol 3'-kinase (PI3K)/Akt signaling.

The discovery of neural stem cells in the adult brain has led to extensive investigation of their potential for promoting endogenous repair following neural injury or disease. Although neural insult alone is sufficient to expand resident NPC populations, and though this process can be augmented with exogenous factors, only a subpopulation of the expanded pool migrate to lesion sites in response to insult. Endogenous neurorepair processes may be enhanced by recruiting greater numbers of NPCs toward insult regions. Balanced biphasic electrical stimulation accomplishes this by selectively targeting and controlling the directed migration of undifferentiated NPCs.

Example 1: Isolation and Culture of Undifferentiated Neural Precursor Cells (NPCs)

NPCs were isolated and cultured using known methods (Reynolds and Weiss, *Science* 255 (5052) 1707-1710, 1992; Richards et al proc. Natl. Acad. Sci. USA 89(18) 8591-8595 (1992); both incorporated herein by reference). Adult male CD1 mice were sacrificed, the periventricular regions of the brain were excised and enzymatically dissociated. Cells were plated in serum free media (SFM) (DMEM:F12 1:1, Invitrogen) supplemented with epidermal growth factor (EGF, 20 ng/mL; Sigma-Aldrich, Canada), basic fibroblast growth factor (bFGF, 10 ng/mL; Sigma-Aldrich, Canada) and heparin (2 μg/mL; Sigma-Aldrich, Canada)—herein referred to as SFM+EFH—at 10 cells/μL in T25 culture flasks (BD Falcon, Canada. After 7 days in culture primary neurospheres (p0) consisting purely of nestin expressing NPCs were collected and plated for electrotaxis experiments or dissociated and re-plated in identical neurosphere forming conditions to form secondary neurospheres (p1). Neurospheres were passaged and plated in mitogenic conditions every 7 days. Neurospheres up to p4 were utilized for experiments.

Example 2: Generation of Suitable Biphasic Electric Field

A Compex Motion electrical stimulator (University of Toronto), (previously described in M. R. Popovic and T. Keller, "Modular transcutaneous functional electrical stimulation system," *Med Eng Phys*, vol. 27, no. 1, pp. 81-92, January 2005, incorporated herein by reference) was utilized to generate the desired electric fields. The Compex Motion provided a portable electrical stimulator, having four current regulated output channels, each of which capable of being independently controlled. The Compex Motion stimulator was used because the output waveforms were easily programmed to a desired output function; any stimulator capable of providing the desired output, as described further below, could be used.

Figure 1A:
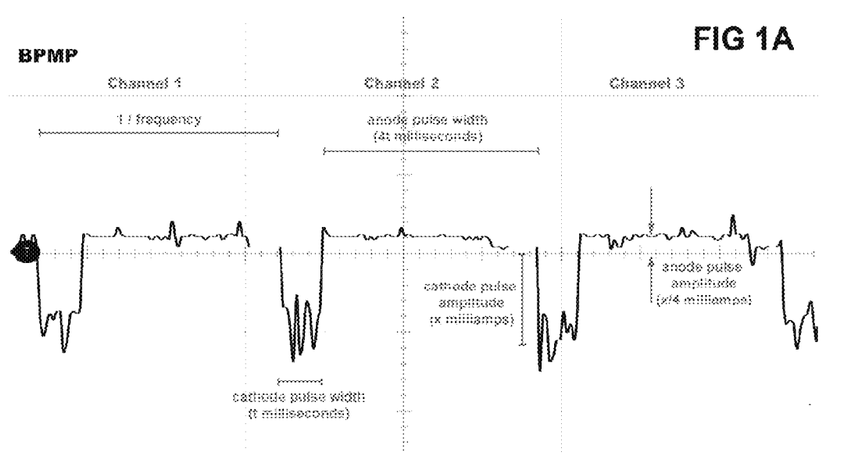
FIG. 1A shows an oscilloscope trace of a representative biphasic monopolar pulse utilized to induce electrotaxis in precursor cells.
Figure 1B:
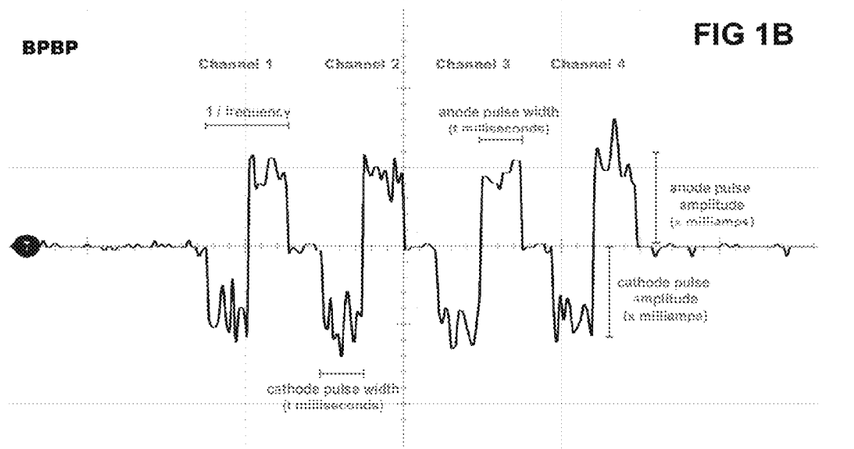
FIG. 1B shows an oscilloscope trace of a representative biphasic bipolar pulse.

The stimulator was programmed to provide a biphasic monopolar (BPMP) electric field having a negative phase of each pulse balanced by a positive phase that was one-quarter the amplitude and four times the duration, as shown schematically in FIG. 1A. In other experiments, the stimulator was programmed to provide a biphasic bipolar (BPBP) electric field, with a negative phase of each pulse balanced by a positive phase that was equal in amplitude and duration but opposite in polarity, as shown schematically in FIG. 1B. Although the Compex Motion stimulator could not do so, other stimulators are known that can also provide an unbalanced biphasic monopolar electric field, having a negative phase of each pulse partially balanced by a positive phase that is one quarter the amplitude and three times the duration, for example, or one third the amplitude and two times the duration, to provide a field that is more balanced than a monophasic monopolar field but not completely balanced. These unbalanced biphasic monopolar electric fields are predicted to provide a slightly more efficient electrotaxis than the biphasic monopolar field, and less side effects than a monophasic monopolar electric field, as explained further, below.

Without being limited by any particular theory, it was believed that there existed a threshold level of current, below which electrotaxis would not be induced. Accordingly, the BPMP waveform was programmed such that the negative (cathodal) phase of the pulse would induce electrotaxis, but the positive (anodal) balancing phase of the pulse would have a current amplitude below this threshold, and would therefore not create an electrotactic effect in the opposing direction. As described further below, a waveform having an anodal balancing phase of one quarter the current amplitude and four times the duration of the cathodal phase was used, but any waveform having one phase above the current threshold for inducing electrotaxis and the opposing phase below said threshold would provide the desired effect. As well, although a 100% balanced waveform was used in the experiments described below, a partially balanced waveform could be used to provide more efficient electrotaxis at the expense of an increase in side effects such as cell and tissue damage.

For the experiments described below, a cathodal phase of 3 mA, with a pulsewidth of 500 microseconds, was used, followed by a balancing anodal phase of 2000 microseconds pulse width and 0.75 mA amplitude, for a total pulse duration of 2500 microseconds. Outputs of the four channels were staggered, as shown in FIG. 1A, to provide a maximum stimulation frequency of 400 Hz. This allowed the cells to receive maximum exposure to the cathodal current without the overlapping of channel outputs.

The electric field experienced by the cells within the chamber during the cathodal phase can be derived by Ohm's law for conductive media:

$$E = \frac{J}{\sigma},$$

where E is the strength of the electric field, J is the current density (total current through the chamber divided by the chamber's cross-sectional area) and σ is the conductivity of the culture medium. A current of 3 mA driven through chambers with cross-sectional area of ~7 mm² (14 mm×~0.5 mm) resulted in a current density of ~0.43 mA/mm². The conductivity of the culture medium at 37° C. was measured as 14.90 mS/cm, or equivalently the resistivity was 671.14 Ωmm. Multiplying the current density by the culture medium's resistivity yielded an electric field strength of ~287 mV/mm.

Example 3: Electrotaxis Chamber Construction

Electrotaxis chambers were constructed using known methods (Babona-Pilipos et al, JoVE (68) e4193, incorporated herein by reference). Square no. 1 glass cover slides (22 mm×22 mm×0.17 mm, VWR, Canada) were acid-washed in HCl overnight, then sealed to the base of 60 mm×15 mm Petri dishes (VWR, Canada) using silicon vacuum grease (VWR, Canada). Other square no. 1 glass slides were then cut into rectangular strips (22 mm×4 mm×0.17 mm), washed with 70% ethanol followed by autoclaved water, and sealed with grease to opposite edges of the square slide in the Petri dish. The resulting central trough measured 22 mm×12 mm×0.5 mm (l×w×h, and accounting for the thickness of the grease). Chambers were UV sterilized, and the central troughs coated with poly-L-lysine (100 µg/mL) for 2 hours at room temperature, followed by 4% (v/v) Matrigel (BD Biosciences, Canada) in SFM for 1 hour at 37° C. Next, 350 µL of either SFM+EFH or SFM supplemented with 1% fetal bovine serum (FBS, Life Technologies, Canada)—herein referred to as SFM+FBS—were added to the central troughs of the chambers with 5-6 neurospheres that were 80-100 µm in diameter. Chambers were then incubated at 37° C., 5% $CO_2$ and 100% humidity. To investigate the electrotaxis of undifferentiated NPCs, neurospheres were plated onto the chambers for 17-20 hours in SFM+EFH to allow the neurosphere cells to adhere to the Matrigel matrix while remaining undifferentiated. In contrast, to investigate the electrotaxis of differentiated NPCs, neurospheres were plated onto the chambers for 72-96 hours in SFM+FBS to allow neurosphere cells to adhere and differentiate into mature neural phenotypes.

Example 4: Galvanotaxis Assay and Immunocytochemistry

Two 15 cm long pieces of PVC tubing (2.38 mm i.d., 3.97 mm o.d., Fisher Scientific, Canada) were filled with 1.5% (w/v) agarose gel. Ag/AgCl electrodes were formed by coiling and immersing two 10 cm pieces of silver wire (Alfa Aesar, USA) in bleach for 20 minutes. A square no. 1 glass cover slide was sealed with grease to the top of the rectangular strips on either side of the trough, creating a central chamber. Strips of grease were used to create pools of media on either side of the central chamber. The electrotaxis chamber was transferred onto the stage of a temperature-, $CO_2$—, and humidity-controlled Zeiss Observer Z1 microscope (Zeiss, Germany) for time-lapse imaging. Two 60 mm×15 mm Petri dishes were placed on the stage—one on either side of the electrotaxis chamber—and filled with 7.5 mL of SFM. The Ag/AgCl electrodes were placed into these adjacent Petri dishes, and all three dishes were bridged with the agarose gel tubes to establish electrical continuity. An electrical stimulator was connected to the Ag/AgCl electrodes for biphasic pulse application.

Time-lapse imaging was performed to record cell migration via Zeiss Axiovision software, at a capture rate of one image per minute, for 2.5-6 hours. At least 45 cells from a minimum of 3 experiments were tracked for each experimental group. Cells were selected for tracking if they were at least one cell body away from the nearest cell, to reduce the likelihood of tracking cells that overlapped at any point during imaging. Cell centroid positions were used for tracking cell migration. The velocity, directedness, and tortuosity of migration were analyzed.

Cells were fixed for 20 minutes at room temperature with 4% paraformaldehyde, then triple washed with phosphate buffered saline (PBS) for 5 minutes each time. Cells were permeabilized for 20 minutes at room temperature with 0.3% Triton X-100, then blocked with 10% normal goat serum (NGS, Jackson Immunoresearch Laboratories, Canada) in PBS for 1 hour at room temperature. Samples were processed with primary antibodies for NPCs (mouse monoclonal anti-Nestin 1:400, Millipore, Canada), neurons (rabbit polyclonal anti-Class III β-Tubulin, Covance, USA), and astrocytes (rabbit polyclonal anti-GFAP 1:500, Sigma, Canada) overnight at 4° C. Samples were triple washed with PBS for 5 minutes, and incubated with appropriate secondary antibodies for 1 hour at 37° C. Secondary antibodies used were Alexafluor 568 (goat anti-mouse 1:400, Life Technologies, Canada), Alexafluor 488 (goat-anti-rabbit 1:400, Life Technologies, Canada), and Alexafluor 488 (goat anti-mouse 1:300, Life Technologies, Canada). Mounting medium containing DAPI (Vector Laboratories, Canada) was used for nuclear staining.

Example 5: Electrotaxis in Undifferentiated NPCs Utilizing BPMP and BPBP Pulses

Neurospheres were prepared as described in Example 1, and plated on the electrotaxis chambers as described in Example 3 and 4 for 17-20 hours in the presence of growth factors (SFM+EFH) to maintain the NPCs in an undifferentiated state. During this period, neurospheres adhered to the Matrigel-coated base of the chambers and dissociated into single cells. The migration of undifferentiated NPCs was then analyzed using time-lapse imaging for a period of 2.5-6 hours in the presence of BPMP or BPBP stimulation utilizing the electric fields generated as described in Example 2, as well as without any applied electric field.

Figure 2:
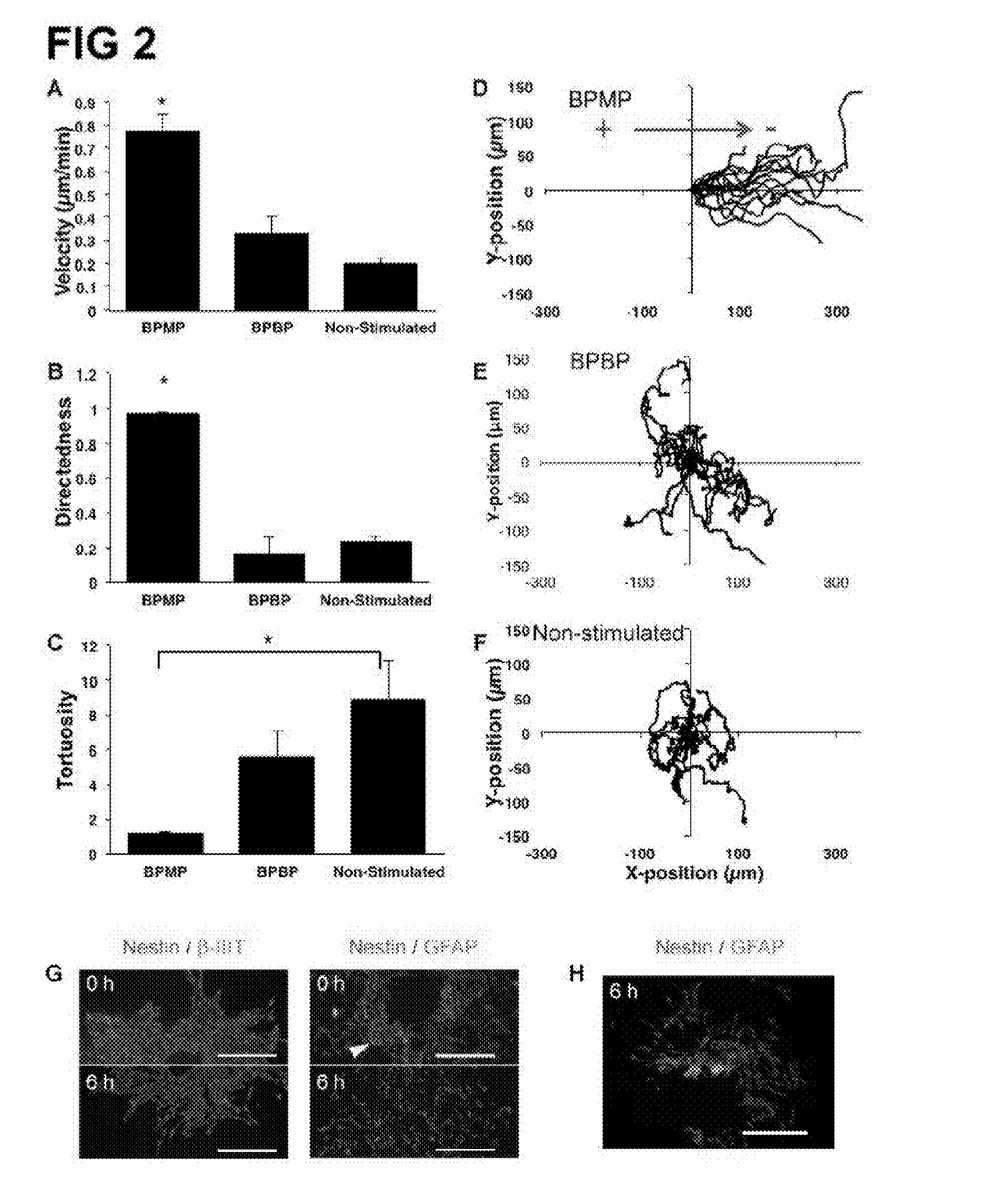
FIG. 2A shows the velocity of undifferentiated neural precursor cells stimulated in vitro with biphasic monopolar and biphasic bipolar electrical stimulation, as compared to non-stimulated cells.
FIG. 2B shows the directedness of undifferentiated neural precursor cells stimulated in vitro with biphasic monopolar and biphasic bipolar electrical stimulation, as compared to non-stimulated cells.
FIG. 2C shows the tortuosity of undifferentiated neural precursor cells stimulated in vitro with biphasic monopolar and biphasic bipolar electrical stimulation, as compared to non-stimulated cells.
FIG. 2D shows individual cell migration tracks localized to a common origin for undifferentiated neural precursor cells subjected in vitro to biphasic monopolar pulses of electrical stimulation.
FIG. 2E shows individual cell migration tracks localized to a common origin for undifferentiated neural precursor cells subjected in vitro to biphasic bipolar pulses of electrical stimulation.
FIG. 2F shows individual cell migration tracks localized to a common origin for undifferentiated neural precursor cells not subjected to electrical stimulation.
FIG. 2G shows that NPCs remain undifferentiated prior to and following exposure to BPMP and BPBP stimulation.
FIG. 2H shows that NPCs remain undifferentiated following a 6-hour imaging period in the absence of electrical stimulation.

In the absence of electrical stimulation, undifferentiated NPCs migrated at a mean velocity (defined as the straight-line distance between initial and final cell positions, divided by total experiment duration) of 0.20±0.02 µm/min (FIG. 2A). Their migration was non-directed, with a mean directedness (defined as the cosine of the angle between the positive X-axis and the straight line between the initial and final cell positions) of 0.23±0.03, and a mean tortuosity (defined as total path length divided by the straight-line distance between initial and final cell positions) of 8.93±2.14 (FIG. 2B, C, F).

Cells exposed to BPBP stimulation exhibited migratory behaviour similar to that of cells not exposed to electrical stimulation, with a mean velocity of 0.33±0.07 µm/min, a mean directedness of 0.16±0.09, and a mean tortuosity of 5.65±1.43 (FIG. 2A-C, E). Strikingly, when undifferentiated NPCs were exposed to BPMP stimulation, they underwent rapid electrotaxis at a rate of 0.77±0.07 µm/min (a significant 2-fold and 3-fold increase as compared to BPBP and non-stimulated groups, respectively, $p<0.05$) (FIG. 2A). The migration of cells in the presence of BPMP stimulation was highly cathodally-directed, with mean directedness of 0.97±0.01 (>8-fold and >4-fold increase compared to BPBP and non-stimulated groups, $p<0.05$) and mean tortuosity of 1.18±0.03 (>7-fold decrease compared to non-stimulated groups, $p<0.05$) (FIG. 2B-C, D). Notably, undifferentiated NPCs exposed to BPMP stimulation migrated at approximately 71% of the velocity and 100% of the directedness of NPCs exposed to dcEFs as previously described, even though BPMP-stimulated cells had only 20% of the exposure to cathodal current as compared to previously-described dcEF stimulated cells. Out of 674 cells analyzed across 3 independent experiments, 95.9%±0.01% of undifferentiated NPCs underwent cathodal electrotaxis in the presence of BPMP stimulation. Hence, undifferentiated NPCs exposed to BPMP pulses undergo rapid and directed electrotaxis toward the cathode, but their migration is slower and non-directed when either exposed to BPBP pulses or in the absence of electrical stimulation.

Pre- and post-imaging immunocytochemical analysis verified that the cells remained nestin+(a marker of undifferentiated NPCs) and did not express neuronal (β-III Tubulin) or glial (GFAP) markers, when maintained in the presence of growth factors, regardless of whether or not they were exposed to biphasic stimulation (FIG. 2G-H). A small subset of cells co-expressed GFAP and nestin (arrowhead in FIG. 2G), and these may represent bona fide type-B neural stem cells.

Figure 3:
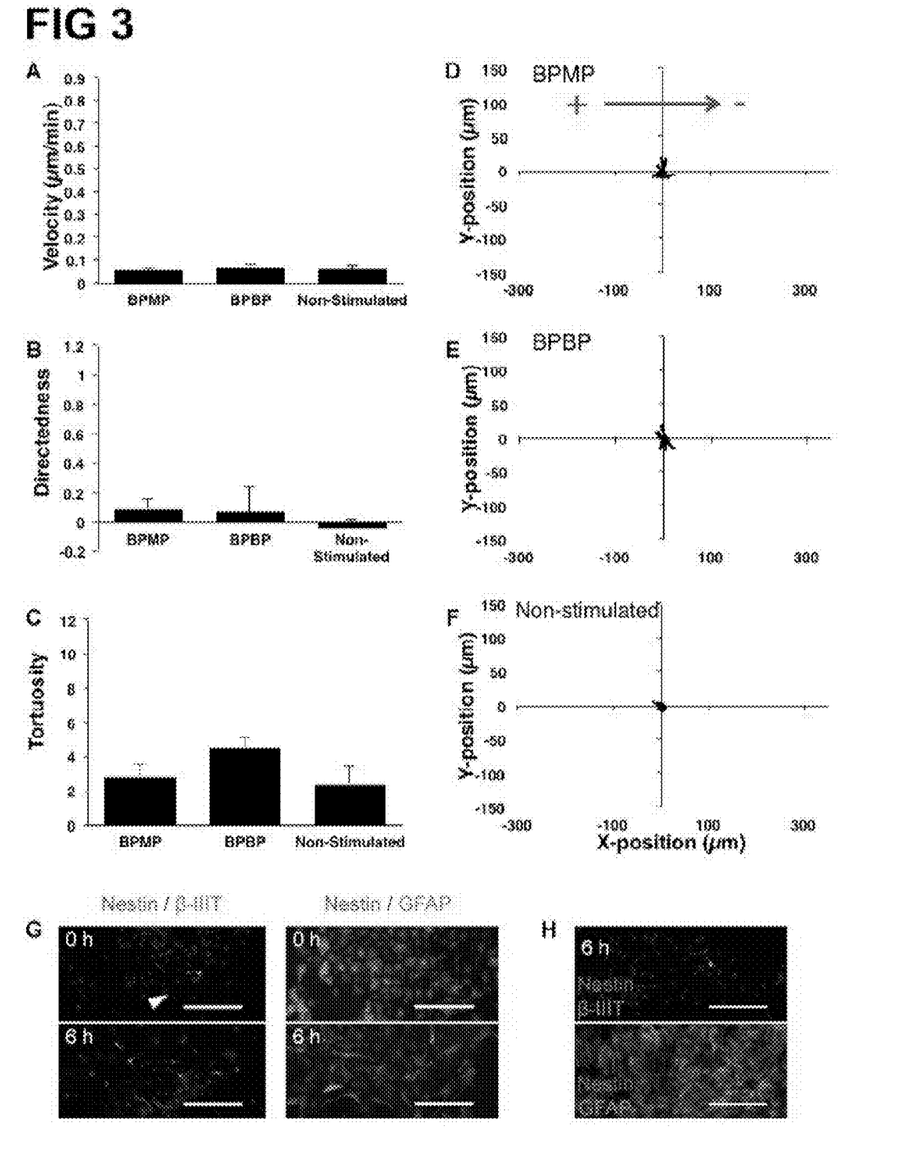
FIG. 3A shows the velocity of differentiated neural precursor cells stimulated in vitro with biphasic monopolar and biphasic bipolar electrical stimulation, as compared to non-stimulated cells.
FIG. 3B shows the directedness of differentiated neural precursor cells stimulated in vitro with biphasic monopolar and biphasic bipolar electrical stimulation, as compared to non-stimulated cells.
FIG. 3C shows the tortuosity of differentiated neural precursor cells stimulated in vitro with biphasic monopolar and biphasic bipolar electrical stimulation, as compared to non-stimulated cells.
FIG. 3D shows individual cell migration tracks localized to a common origin for differentiated neural precursor cells subjected in vitro to biphasic monopolar pulses of electrical stimulation.
FIG. 3E shows individual cell migration tracks localized to a common origin for differentiated neural precursor cells subjected in vitro to biphasic bipolar pulses of electrical stimulation.
FIG. 3F shows individual cell migration tracks localized to a common origin for differentiated neural precursor cells not subjected to electrical stimulation.
FIG. 3G shows that NPCs induced to differentiate maintain expression of neuronal and astrocytic markers prior to and following exposure to BPMP stimulation.
FIG. 3H shows that NPCs induced to differentiate maintain expression of neuronal and astrocytic markers following a 6-hour period of imaging in the absence of electrical stimulation.

Example 6: No Electrotaxis in Differentiated NPCs Utilizing BPMP and BPBP Pulses Neurospheres (P0-P4) were plated onto Matrigel-coated electrotaxis chambers in the presence of 1% FBS for 72-96 hours to induce cell differentiation. Differentiated cells were maintained in 1% FBS conditions and time-lapse imaged for 2.5-6 hours while either stimulated with BPMP or BPBP pulses, or not stimulated. Differentiated cells did not undergo electrotaxis neither in the presence nor the absence of biphasic stimulation (both BPMP and BPBP modes). Their velocity (BPBP: 0.07±0.01 μm/min, BPMP: 0.05±0.01 μm/min), directedness (BPBP: 0.07±0.09, BPMP: 0.09±0.04) and tortuosity (BPBP: 4.53±0.33, BPMP: 2.85±0.40) of migration did not significantly differ from that of non-stimulated differentiated cells (velocity: 0.06±0.01 μm/min, directedness: −0.04±0.03, tortuosity: 2.39±0.58) (FIG. 3A-F). Immunocytochemical analysis verified that the cells had differentiated into $GFAP^+$ astrocytes and $βIII$-$Tubulin^+$ neurons prior to time-lapse imaging, and their mature phenotypes were maintained after 6 hours of imaging in the presence of absence of biphasic stimulation (FIG. 3G-H). Biphasic stimulation thus did not induce electrotaxis in differentiated neural cells, and as such, provided selective electrotaxis for undifferentiated NPCs only.

Example 7: In Vivo Electrotaxis of Transplanted Undifferentiated NPCs

Figure 4:
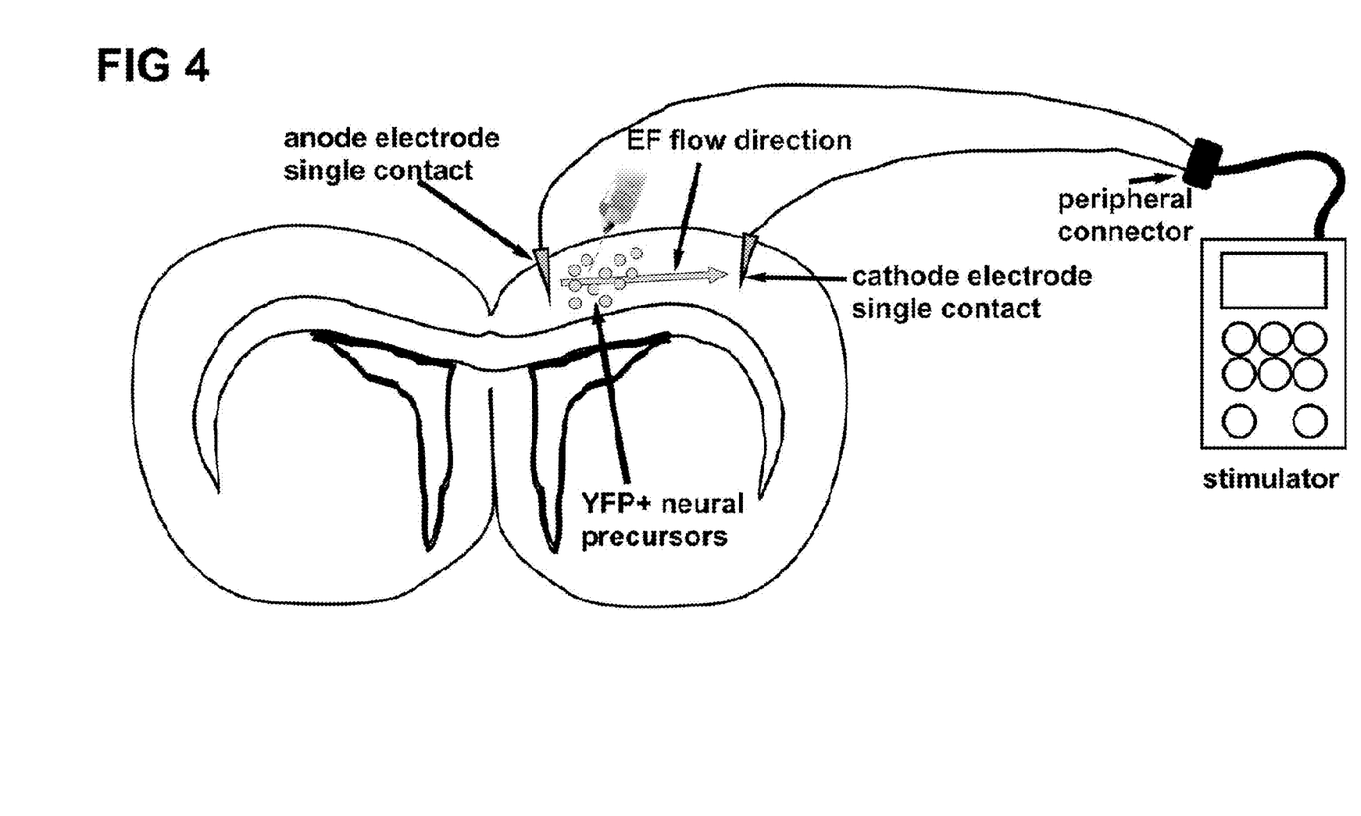
FIG. 4 shows a schematic of a biphasic stimulator with connected single-contact electrodes implanted into a non-injured rodent brain that has been injected with YFP+ neural precursors.
Figure 5:
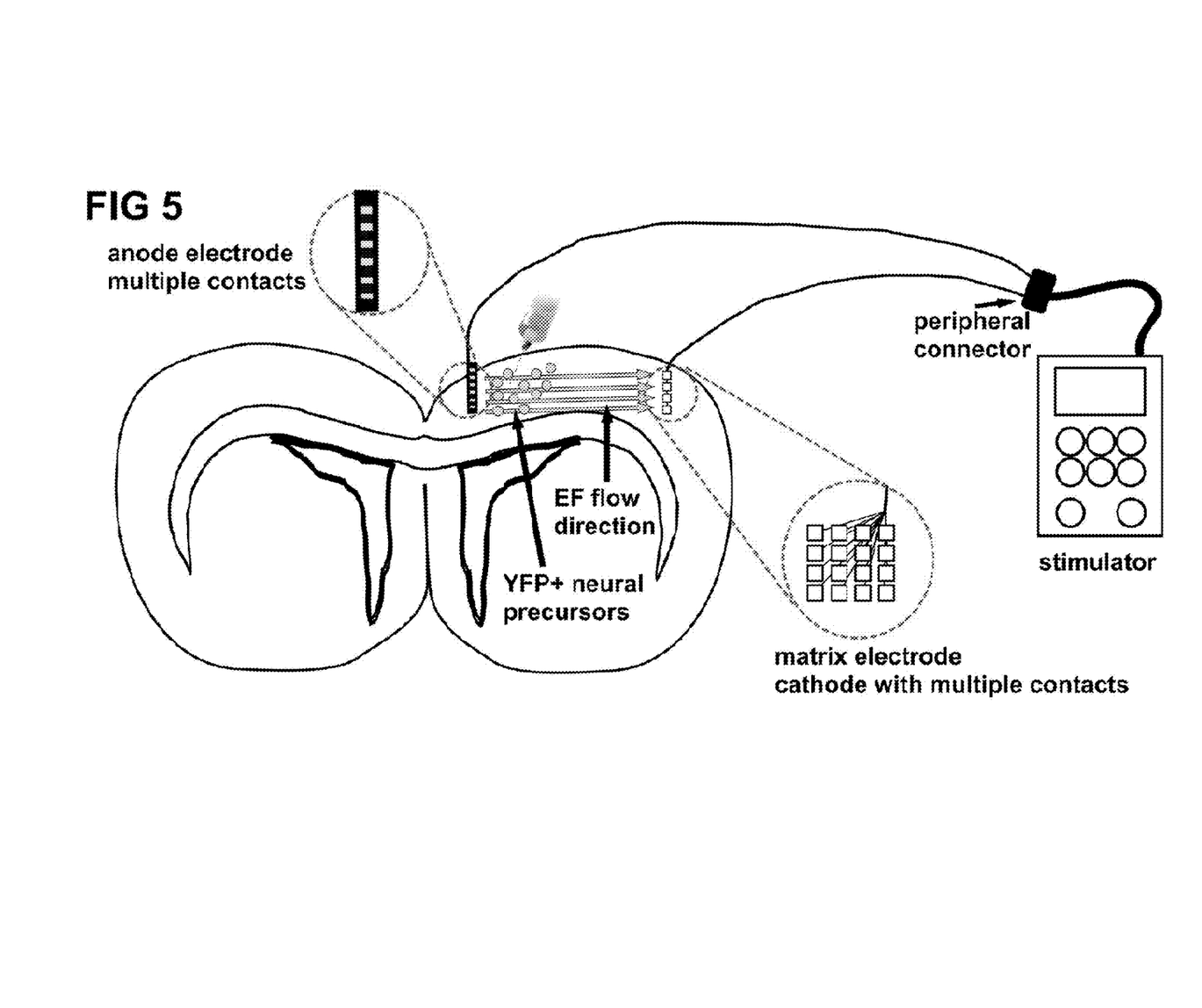
FIG. 5 shows a schematic of a biphasic stimulator with connected multiple-contact electrodes implanted into a non-injured rodent brain that has been injected with YFP+ neural precursors.

The electrical stimulation described herein is utilized to migrate transplanted, undifferentiated NPCs from the site of transplantation in the brain to a distal parenchymal region. Neural precursor cells, prelabeled with a fluorescent marker, are isolated, using the methods of Example 1. Note that the cells are prelabeled by utilizing transgenic mice expressing yellow-fluorescent protein (YFP+ precursors). YFP+ precursors are transplanted into the striatum, corpus callosum, or cortex of non-injured adult CD1 mice. At the time of transplantation, stimulation electrodes are also implanted intracranially into the brain parenchyma, positioned along the mediolateral axis at the following stereotaxic coordinates: anode—bregma AP+0.7 mm, ML+0.7 mm, DV −2.5 mm, cathode—bregma AP+0.7 mm, ML+1.7 mm, DV −2.5 mm. The electrodes interface with an external biphasic stimulator through a peripheral connector. Either single contact (FIG. 4) or multiple contact (FIG. 5) electrodes can may utilized. In the single contact configuration, a single electric field waveform is delivered. In the multiple contact configuration, several different waveforms can be implemented, each with its own stimulation parameters, resulting in multiple stimulation channels that can each be controlled independently. Stimulation is initiated one day post-transplantation, and is applied three times daily for 15 minutes per application utilizing the following parameters: 0.5-5 mA amplitude, 100-500 μs pulse width, 100-400 Hz frequency, while maintaining the charge density within the safety margin of 170-480 $C/m^2$. Animals are allowed to move freely within their cages during biphasic stimulation. At 1, 2, 4 or 7 days post-stimulation, animals are sacrificed, and brains are excised, sectioned and immunostained to analyze the numbers, location and phenotypes of transplanted $YFP^+$ neural precursors as well as stained for markers of cell death and inflammation, and compared to control groups (mice with transplants but no stimulation, and mice receiving stimulation but without transplanted cells). The labeled NPCs are found to migrate directionally through the electric field, toward the cathode electrode. Brain tissue exhibits minimal and statistically insignificant damage in the electric field area.

Figure 6:
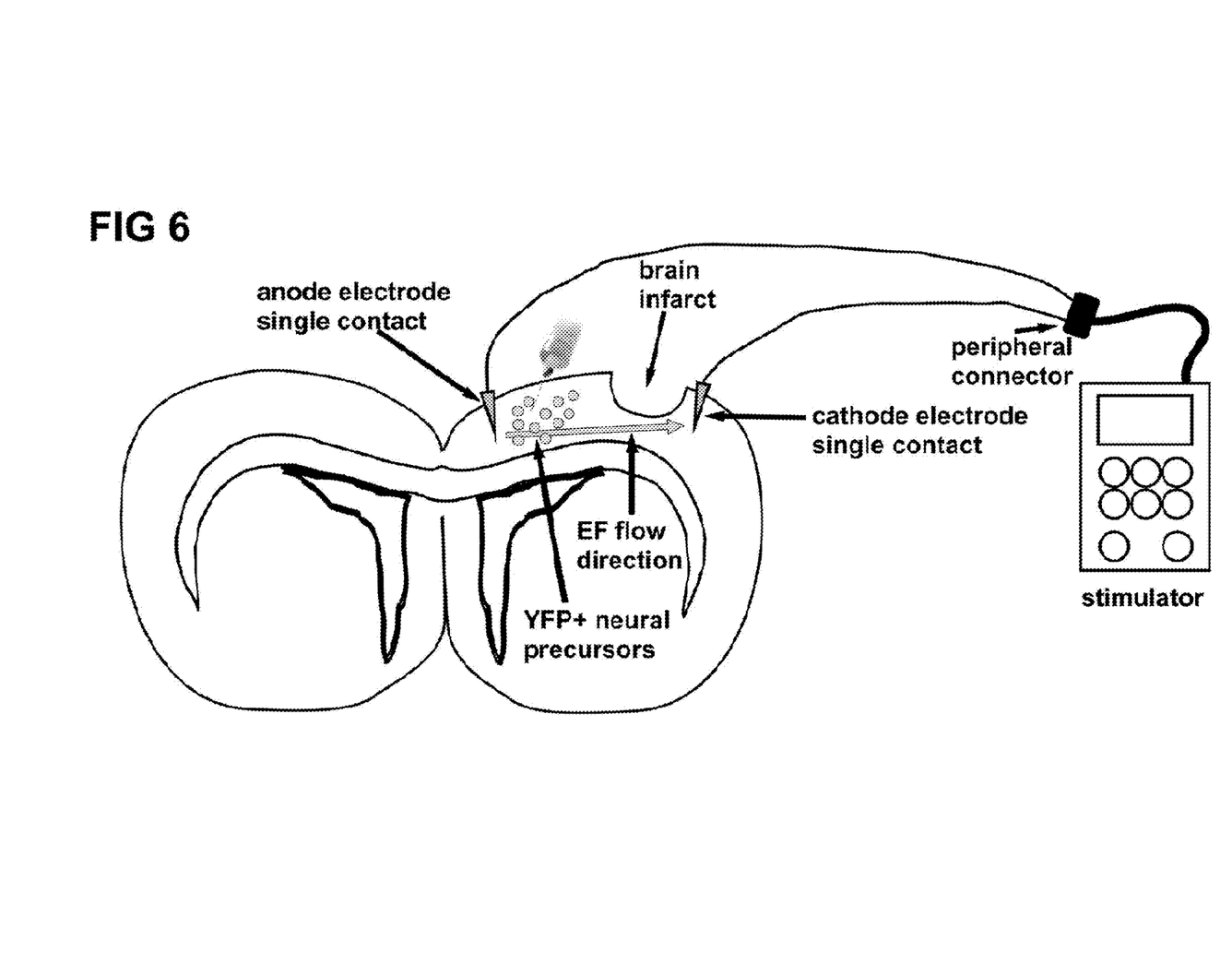
FIG. 6 shows a schematic of a biphasic stimulator with connected single-contact electrodes implanted into a stroke-injured rodent brain that has been injected with YFP+ neural precursors.
Figure 7:
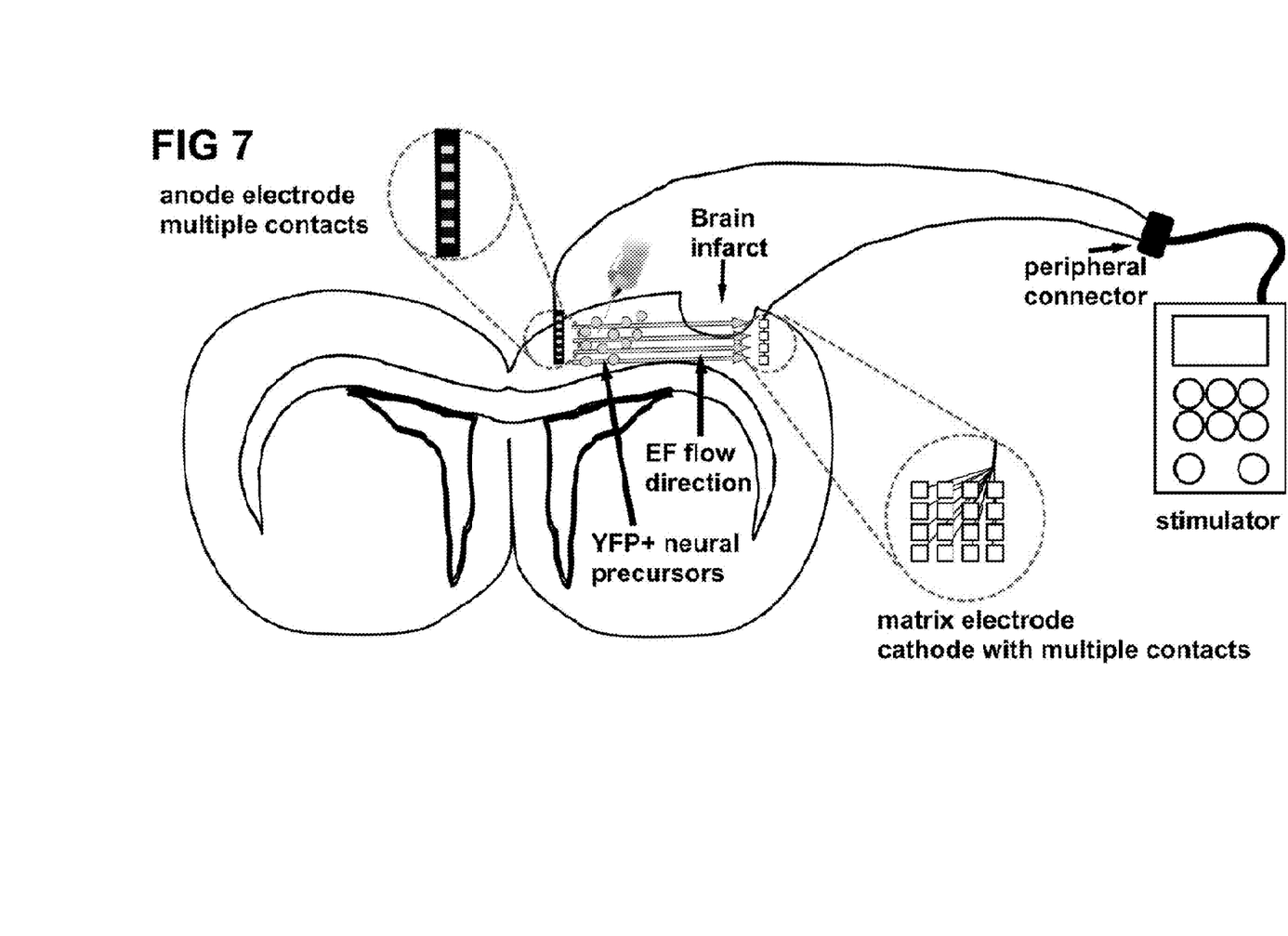
FIG. 7 shows a schematic of a biphasic stimulator with connected multiple-contact electrodes implanted into a stroke-injured rodent brain that has been injected with YFP+ neural precursors

Example 8: In Vivo Electrotaxis of Transplanted Undifferentiated NPCs to Repair the Injured Brain The electrical stimulation described herein is utilized to migrate transplanted, undifferentiated NPCs from the site of transplantation in the brain to the site of an induced injury in the brain. Neural precursor cells, prelabeled with a fluorescent marker, are isolated using the methods of Example 1. Note that the cells are prelabeled by utilizing transgenic mice expressing yellow-fluorescent protein (YFP+ precursors). Animals are anesthetized and provided a stroke lesion via endothelin-1 injections into the motor cortex (bregma AP+0.6 mm, ML+2.25 mm, DV −0.6 mm). YFP+ precursors are transplanted medial to the injury site at the time of injury. At the time of transplantation, stimulation electrodes are also implanted intracranially into the brain parenchyma, positioned along the mediolateral axis such that the anode is medial to the YFP+ precursor transplantation site, and the cathode is lateral to the injury site. The electrodes interface with an external biphasic stimulator through a peripheral connector. Either single contact (FIG. 6) or multiple contact (FIG. 7) electrodes can may utilized. In the single contact configuration, a single electric field waveform is delivered. In the multiple contact configuration, several different waveforms can be implemented, each with its own stimulation parameters, resulting in multiple stimulation channels that can each be controlled independently. Stimulation is initiated one day post-transplantation, and is applied three times daily for 15 minutes per application utilizing the following parameters: 0.5-5 mA amplitude, 100-500 μs pulse width, 100-400 Hz frequency, while maintaining the charge density within the safety margin of 170-480 $C/m^2$. Animals are allowed to move freely within their cages during biphasic stimulation. At 2, 7, 14 and 32 days post-stimulation, animals are sacrificed, and brains are excised, sectioned and immunostained to analyze the numbers, location and phenotypes of transplanted $YFP^+$ neural precursors, and compared to control groups (mice with transplants but no stimulation, and mice receiving stimulation but without transplanted cells). Behavioural assays (such as cylinder task and foot fault task) for motor recovery are performed at all time points to measure functional improvement. Infarct sizes of the lesion site are measured and the contribution of YFP+ precursors or their progeny to new tissue is analyzed. The labeled NPCs are found to migrate directionally through the electric field, toward the cathode electrode into the injury site, where they contribute to neural tissue regeneration. Brain tissue exhibits minimal and statistically insignificant damage in the electric field area.

Example 9: Isolation and Culture of Undifferentiated Skin Derived Precursors

Skin derived precursors are isolated and cultured using known methods (Bernaskie et al Nat Protoc. 1(6) 2803-2812

(2006); incorporated herein by reference). Adult male CD1 mice are sacrificed, their back fur is shaved, a rectangle of dorsal back skin is dissected from the middle of the back, minced and enzymatically dissociated using collagenase. Cells are then further mechanically dissociated and filtered through a cell strainer. Cells are plated in serum free media (SFM) (DMEM+Glutamax:F12 3:1, Invitrogen) supplemented with epidermal growth factor (EGF, 20 ng/mL; Sigma-Aldrich, Canada), basic fibroblast growth factor (bFGF, 40 ng/mL; Sigma-Aldrich, Canada) and 2% B27 supplement (Sigma-Aldrich, Canada)—herein referred to as SFM+EF—at 10 cells/µL in T25 culture flasks (BD Falcon, Canada. After 7 days in culture primary skin derived precursor spheres (p0) are collected and plated for electrotaxis experiments or dissociated and re-plated in identical proliferative conditions to form secondary skin derived precursor spheres (p1). Spheres are passaged and plated in mitogenic conditions every 7-10 days.

Example 10: In Vivo Electrotaxis of Transplanted Undifferentiated Skin Derived Precursors for Cutaneous Wound Repair The electrical stimulation described herein is utilized to migrate transplanted, undifferentiated skin derived precursors from the site of transplantation in the skin to the site of an induced cutaneous injury. Skin derived precursor cells, prelabeled with a fluorescent marker, are isolated, using the methods of Example 9. Note that the cells are prelabeled by utilizing transgenic mice expressing yellow-fluorescent protein (YFP+ precursors). Animals are to be anesthetized and provided a cutaneous wound using a biopsy punch and surgical scissors to create circular wounds on the ventral back of the mice. YFP+ precursors are to be transplanted adjacent to the injury site at the time of injury. At the time of transplantation, stimulation electrodes are also applied to the surface of the skin using adhesive patches such that the anode is medial to the YFP+ precursor transplantation site, and the cathode is lateral to the injury site. The electrodes will interface with an external biphasic stimulator through a custom-designed peripheral connector. Stimulation is initiated one day post-transplantation, and is applied three times daily for 15 minutes per application utilizing the following parameters: 0.5-5 mA amplitude, 100-500 µs pulse width, 100-400 Hz frequency, while maintaining the charge density within the safety margin of 170-480 C/m². Animals are allowed to move freely within their cages during biphasic stimulation. At 1, 2 or 4 days post-stimulation, animals are sacrificed, and skin tissue is excised and immunostained to analyze the numbers, location and phenotypes of transplanted YFP+ skin derived precursors, and compared to control groups (mice with transplants but no stimulation, and mice receiving stimulation but without transplanted cells). Wound sizes are measured and the contribution of YFP+ precursors or their progeny to new tissue is analyzed. The labeled skin derived precursors are found to migrate directionally through the electric field, toward the cathode electrode into the injury site, where they contribute to cutaneous tissue regeneration. Cutaneous tissue exhibits minimal and statistically insignificant damage in the electric field area as revealed by immunohistochemistry for markers of cell death and inflammation.

Example 11: Electrotaxis in Undifferentiated Human Neuralized Precursors

Human neuralized precursor cells will be obtained from New World Laboratories Inc (herein referred to as NWL). NWL's human neuralized precursors are obtained from a patient's own somatic cells, and reprogrammed into undifferentiated neuralized precursors using NWL's proprietary methods. Human neuralized precursors will be prepared similar to the methods described in Example 1, and plated on the electrotaxis chambers as described in Example 3 and 4 for 5-20 hours in the presence of growth factors (SFM+EFH) to maintain the neuralized precursor cells in an undifferentiated state. During this period, neuralized precursors adhere to the basement membrane-coated base of the chambers. The migration of undifferentiated neuralized precursors is analyzed using time-lapse imaging for a period of 2.5-6 hours in the presence of BPMP or BPBP stimulation utilizing the electric fields generated as described in Example 2, as well as without any applied electric field.

In the absence of electrical stimulation, undifferentiated neuralized precursors are expected to migrate in a non-directed manner. Cells exposed to BPBP stimulation are expected to exhibit migratory behaviour similar to that of cells not exposed to electrical stimulation. Undifferentiated neuralized precursors exposed to BPMP stimulation are expected to undergo rapid electrotaxis toward the cathode terminal.

Pre- and post-imaging immunocytochemical analysis is performed to verify that the cells express markers of undifferentiated neural precursors when maintained in the presence of growth factors, regardless of whether or not they were exposed to biphasic stimulation.

The invention claimed is:

1. A method of enhancing migration of a precursor cell in a desired direction, comprising applying a biphasic monopolar electrical field having a cathode end and an opposing anode end to said precursor cell, wherein the biphasic monopolar electrical field is a charge balanced biphasic monopolar electrical field.

2. The method of claim 1 wherein the balanced biphasic monopolar electrical field comprises a negative phase and a positive phase, wherein the negative phase has a greater amplitude than the positive phase, and the positive phase has a greater duration than the negative phase, charge-balancing said greater amplitude of said negative phase.

3. The method of claim 2 wherein the negative phase and the positive phase are pulsatile phases.

4. The method of claim 2 wherein the negative phase and the positive phase are constant phases.

5. The method of claim 2 wherein the negative phase has an amplitude of between 2 to 5 mA and a pulse width of between 250 to 750 µs.

6. The method of claim 2 wherein the negative phase yields an electric field strength of less than 500 mV/mm.

7. The method of claim 2 wherein the charge balanced biphasic monopolar electrical field has a frequency of between 100 to 1000 Hz.

8. A system for performing the method of claim 2, comprising:
   a. an electrical stimulator configured to provide the balanced biphasic monopolar electrical field having the negative phase having a greater amplitude than the positive phase, and the positive phase with a greater duration than the negative phase, charge-balancing said greater amplitude of said negative phase;
   b. at least one anode connected to said stimulator by an electrical cable;
   c. at least one cathode connected to said stimulator by an electrical cable;
   whereby the anode and cathode are capable of being applied to said respective anode end and cathode end to provide the biphasic monopolar electrical field and enhancing the migration of the precursor cell.

9. The method of claim 5 wherein the charge balanced biphasic monopolar electrical field comprises a negative phase and a positive phase, wherein the positive phase has a greater amplitude than the negative phase, and the negative phase has a greater duration than the positive phase, charge-balancing said greater amplitude of said positive phase.

10. The method of claim 9 wherein the positive phase has an amplitude of between 2 to 5 mA and a pulse width of between 250 to 750 μs.

11. The method of claim 9 wherein the positive phase yields an electric field strength of less than 500 mV/mm.

12. The method of claim 1 wherein the biphasic monopolar electrical field is an unbalanced biphasic monopolar electrical field.

13. The method of claim 1 wherein the migration is specific to undifferentiated neural precursor cells, such that differentiated cells do not migrate in said desired direction when the field is applied.

14. The method of claim 1 wherein the method comprises applying the electrical field through a portion of a central nervous system.

15. A system for performing the method of claim 1, comprising:
   a. an electrical stimulator configured to provide the biphasic monopolar electrical field;
   b. at least one anode connected to said stimulator by an electrical cable;
   c. at least one cathode connected to said stimulator by an electrical cable;
   whereby the anode and cathode are capable of being applied to said respective anode end and cathode end to provide the biphasic monopolar electrical field and enhancing the migration of the precursor cell.

16. The method of claim 1 wherein the desired direction is generally in the direction of the electrical field.

17. The method of claim 1 wherein the desired direction is independent of an existing biological and/or pathological pathway.

18. A method of treating a disease or injury of a central nervous system of a patient, comprising:
   a. determining a location of an injured region within said central nervous system;
   b. determining a location of a source of neural precursor cells in said central nervous system;
   c. applying electrodes to said patient such that the distance between said electrodes form a path, said path transecting both the location of the source of neural precursor cells and the location of the injured region;
   d. Applying the method of claim 1 to said central nervous system.

19. The method of claim 18 wherein the portion of the central nervous system being applied to is the brain.

20. A method of treating a disease or injury of the skin tissue of a patient, comprising:
   a. determining a location of an injured region within said skin tissue;
   b. determining a location of a source of precursor cells in or proximal to said skin tissue;
   c. applying electrodes to said patient such that the distance between said electrodes form a path, said path transecting both the location of the source of precursor cells and the location of the injured region;
   d. Applying the method of claim 1 to said skin tissue.

* * * * *